United States Patent [19]

Cavazza

[11] 4,130,116
[45] Dec. 19, 1978

[54] POCKET INHALATOR

[75] Inventor: Claudio Cavazza, Rome, Italy

[73] Assignee: Sigma Tau S.p.A. Industrie Farmaceutiche Riunite, Italy

[21] Appl. No.: 816,178

[22] Filed: Jul. 15, 1977

[30] Foreign Application Priority Data

Aug. 13, 1976 [IT] Italy ................................ 50904 A/76

[51] Int. Cl.² ........................................... A61M 15/00
[52] U.S. Cl. ................................ 128/203; 128/173 R; 222/534; 222/535
[58] Field of Search .................... 128/203, 173 R, 208; 222/193, 526, 533, 534, 535, 538

[56] References Cited

U.S. PATENT DOCUMENTS

| 3,157,179 | 11/1964 | Paullus et al. | 128/208 X |
| 3,739,950 | 6/1973 | Gorman | 128/173 R X |

Primary Examiner—Henry J. Recla
Attorney, Agent, or Firm—McGlew and Tuttle

[57] ABSTRACT

A hollow device which can be easily carried in a pocket or purse and in which can be inserted a spray can used to carry substances for inhalation. Mechanical means are provided wherein the device is kept in a closed position when not in use but can be easily activated to expose the nozzle portion of the spray can to permit utilization of the can.

4 Claims, 4 Drawing Figures

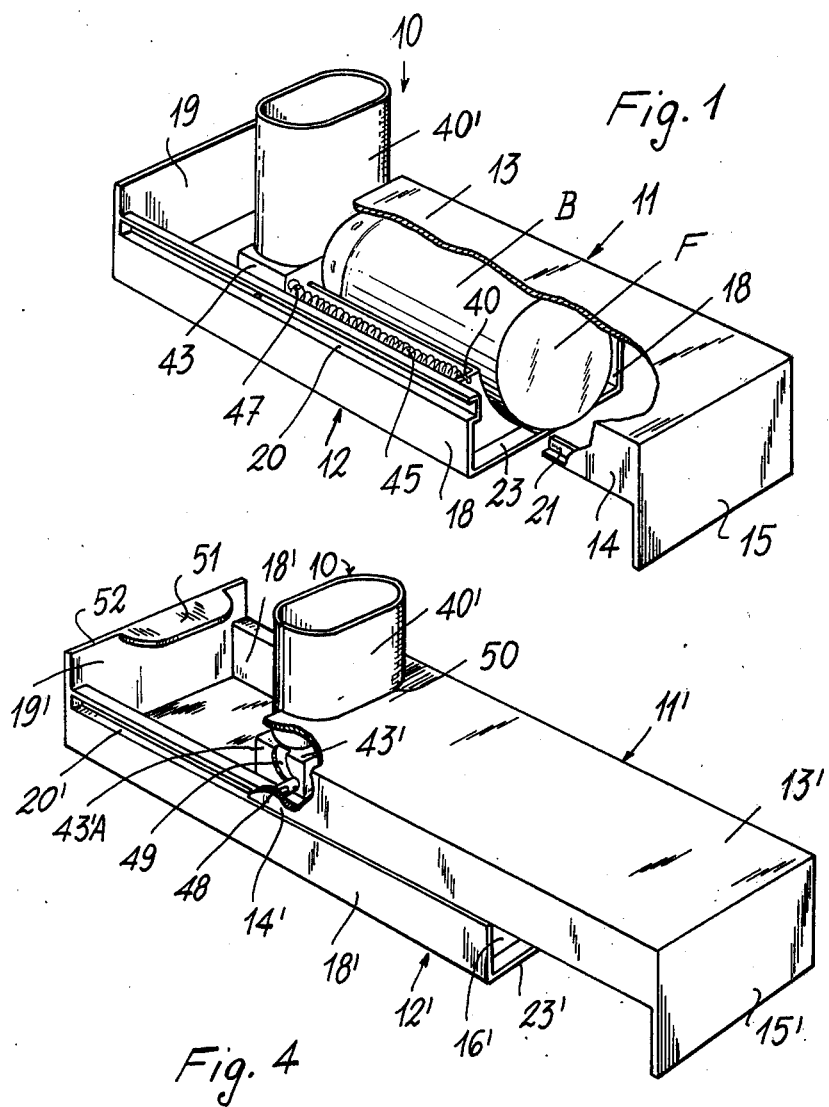

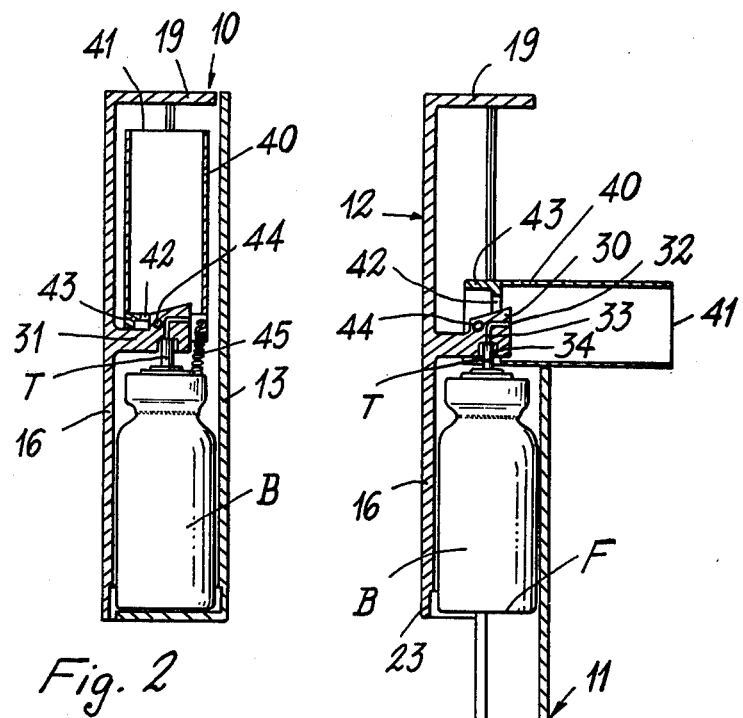

POCKET INHALATOR

The present invention relates to a pocket device apt to hold a spray can.

Many people such as, for example, those suffering from asthma, must treat themselves hourly by inhalation of the suitable medicinal substance and, at present, the inhalation devices for such substances consist of spray cans having a tubular nozzle of a suitable material, either plastic or metallic.

However, such devices are not in an advanced development stage and, furthermore, present many practical inconvenients due to the fact that said device must be carried by the user either in a pocket or in a pocketbook and therefore the condition is aggravated by the problem of keeping the nozzle in good hygienic conditions and also by the problem of protecting the contents thereof against damages or breakage.

The object of the present invention is that of avoiding said problems by providing an inhalation device to be carried in a pocket or in a purse and also which receives within the inside thereof the spray can, which, in the non-operating position, is normally closed with respect to the nozzle, whereas, in the operating position, automatically places the nozzle in the operating position and exposes the spray can to permit the actioning thereof and the consequent dispensing of the medicinal substance through said nozzle.

Said inhalator consists of an elongated hollow body having on the interior thereof, spray means connectable to the discharge means of the spray can when said can is inserted within said hollow body, and a nozzle connected with said nozzle nest completely within said hollow boby and a use position, to which said nozzle moves automatically when said hollow body is opened.

Furthermore, when the hollow body is in the open position, it is extremely easy to replace the exhausted spray can.

The invention will now be described in more detail with reference to the attached drawings in which:

FIG. 1 is a prospective view of a first embodiment of the present invention;

FIG. 2 is a sectional view, on a reduced scale, of the inhalator of FIG. 1 in its rest position;

FIG. 3 is a similar sectional view of the inhalator in its operating position;

FIG. 4 is a prospective view of a second embodiment of the invention.

With reference to FIGS. 1, 2 and 3, inhalators according to the invention consists essentially of a hollow body or container 10, spraying means 30 supported within the interior of said body 10; and an inhalation nozzle 40 supported on the inside of body 10 in connection with spraying means 30 which is able to rotate from the position illustrated in FIG. 2 to that illustrated in FIG. 3.

The body 10, which is in the shape of a parallelogram as illustrated in the drawings, consists of a first half 11 and by a second half 12.

The first half 11 consists of an external wall 13, two lateral walls 14, and an end wall 15.

The second half 12 is correspondingly composed of an external wall 16, two lateral walls 18, and an end wall 19.

The half 12 carries thereon grooved guiding means 20 located along the borders of the lateral walls 18 on which are engaged tracked guide means 21 attached along the sides of the lateral walls 14 of the half 11 so that the two halves may slide with respect to each other within said guides to permit the opening and the closing of container 10.

With half 12 there is intergral a section (FIGS. 2 and 3) on which are carried spraying means 30 consisting of a spraying head having a lateral spray nozzle 32 and an axial channel 33, communicating with spray nozzle 32, which is furnished with a blind end 34 at its lower open extremity.

The nozzle 40 consists of a sleeve open at 41 at its outside end and at 42 at its inside end with which is integral with a bridged base 43 hinged on section 31 by means of a pivot 44 in a manner that the complex nozzle-base can rotate around it so that the head 30 finds itself in correspondence with the internal opening 42 of nozzle 40.

To obtain an automatic passage of nozzle 40 from the rest position to the operating position when the inhalator is opened, in the embodiments of FIGS. 1, 2 and 3, there is provided an helicoidal tensioned spring 45, anchored at one of its end to base 43 at point 47 of nozzle 40 and at the other end by hook 46 to part 12A which is integral with half 12.

Since the anchoring point 47 of spring 45 on base 43 is offset with respect to the axis of rotation 44 of the nozzle, it will tend to make it rotate around said axis so that, when the two halves are opened, under the action of spring 45 nozzle 40 will snap from its rest position illustrated in FIG. 2 to the operating position illustrated in FIGS. 1 and 3.

The position of the spray can on the inside of the inhalator according to the invention is clearly illustrated in the drawings.

As to the substitution it is sufficient to slide out the used can and to insert another one in its place with the dispensing tube T nesting in the lower blind end 34 of channel 33. While there can be provided means comprising an elastic blade of friction means, normally it is sufficient to this end to hold the can by the friction between the outer cylindrical surface of the can and the internal surfaces of the walls of container 10 and the dispensing tube T on the inside of blind-end 34.

Obviously, for use, one must open the container 10 making the two halves 11, 12 slide one with respect to the other, place nozzle 40 near the mouth which has automatically snapped into an operating position, and then exert pressure with finger on bottom F of the spray can B through the access passage 22 formed between the lower edge 23 of half 12 and the bottom wall 15 of half 11. The pressure exerted will cause a relative axial movement between tube T of can B which rests against the blind end 34 of channel 33 and the body of the same, with a resulting dispensing of the contents of the can through conduits 33 and 32 and nozzle 40.

As is seen, the invention fully achieves the scope of providing a practical and compact inhalator, easy to use, which in addition offers an excellent mechanical and hygienic protection both to the nozzle and to the spray, assured by the lateral walls and by the extremities of the halves 11, 12.

FIG. 4 shows a second embodiment of the invention and in said figure to similar parts have been given the same reference numerals used in FIGS. 1, 2 and 3 with primes.

In this figure, there is a different mode of disposition of the means which automatically carry the inhalation nozzle to the operating position where the container is opened.

As is clearly shown, such means consist of a pivot 48 carried by the interior wall 11A of half 11' to slide, during the sliding operation of said half with respect to half 12'; into the curved groove 49 formed in the corresponding lateral wall 43'A of base 43' of nozzle 40. Said positioning is repeated in the opposite lateral walls of half 12' and of base 43' (not shown in the figure).

Therefore, since in order to actionate nozzle 40', the lateral wall 14' carrying pivot 48 cannot descend below base 43' in the open position, on the lower edge thereof there is formed semicircular groove 50 to receive nozzle 40' in such a position as to permit a complete rotation. The groove 50 evidently necessitates the presence of a making tab element 51 integral with border 52 of wall 19', and 90° from same, which serves to close such groove in the closed position of the inhalator.

In accordance with the present embodiment, the nozzle 40' will find itself automatically in the rest position when the container is closed and in the operating position when the container is open.

As to the materials, all the component parts of the inhalator of the present invention can be constructed from any suitable rigid material, such as aluminium, plastic materials, and the like.

It is understood that the embodiments of the invention illustrated and described can be suitably changed or modified without departing from the ambit or concept of the present invention.

What is claimed is:

1. An inhalator for spray substances contained in a spray can having a dispensing tube, wherein said inhalator comprises:
   (a) a hollow elongated container adapted to contain said spray can in an operating position, said container being formed by a first and a second half, each having lateral walls and only one terminal wall;
   (b) companion guide means with sliding engagement means formed on the sides of said lateral walls of the two halves, adapted to permit a relative limited sliding movement of one of said walls with respect to the other form a first position wherein the container is closed to a second position wherein the container is open and viceversa;
   (c) spraying head means supported by a section integral with said first half having a lateral spray nozzle and an longitudinal axial channel communicating with said nozzle said channel including means adapted, to receive with a certain degree of friction said dispensing tube of the spray can;
   (d) a sleeved nozzle open at its extremity having a bridged base supported by hinged means on said spraying head means such as to be able to rotate between a rest position, in which the axis of the sleeve is parallel to the axis of the elongated container, and an operating position perpendicular to the rest position, wherein the base of said sleeved nozzle is located adjacent said lateral said lateral spray nozzle; and
   (e) mechanical actioning means adapted to bring said sleeved nozzle from said rest position to said operating position when said first and second halves are moved to said second position.

2. An inhalator according to claim 1, wherein said mechanical actioning means for the sleeve nozzle consist of preset elastic means acting in traction, such as a helicoidal spring, having one extremity anchored to said second half and the other extremity anchored to said base of the sleeved nozzle in an offset position with respect to the axis of rotation about said hinged means.

3. An inhalator according to claim 1, wherein said mechanical actioning means for the sleeved nozzle consist of pivots each of which is oppositely located and integral with a lateral wall of said second half and of two curved grooves having an open upper extremity, each formed on a lateral wall of said base of the sleeved nozzle each said upper extremity being in alignment with each said respective pivot, such as that in the final relative sliding opening stage of one half with respect to the other said half said pivots slide into the corresponding curved grooves, forcing said base, and therefore the sleeved nozzle, to consequently rotate laterally with respect to said container.

4. An inhalator acoording to claim 3, wherein on the upper border of the lateral wall of said second half there is formed recess means adapted to receive the sleeved nozzle in the operating position with respect to the rest position and in which on said end wall of said first half there is positioned tab means extending laterally therefrom, said recess means and said tab means being complimentally shaped with respect to each other whereby, said tab means is received in said recess means when said first and second halves are in said first position.

* * * * *